(12) United States Patent
Barthold

(10) Patent No.: US 10,898,359 B2
(45) Date of Patent: Jan. 26, 2021

(54) BALLOON CATHETER

(71) Applicant: JOTEC GmbH, Hechingen (DE)

(72) Inventor: Franz-Peter Barthold, Balingen (DE)

(73) Assignee: JOTEC GMBH, Hechingen (DE)

( * ) Notice: Subject to any disclaimer, the term of this patent is extended or adjusted under 35 U.S.C. 154(b) by 187 days.

(21) Appl. No.: 15/870,726

(22) Filed: Jan. 12, 2018

(65) Prior Publication Data

US 2018/0133042 A1  May 17, 2018

Related U.S. Application Data

(63) Continuation of application No. PCT/EP2016/066581, filed on Jul. 13, 2016.

(30) Foreign Application Priority Data

Jul. 13, 2015 (DE) .......................... 10 2015 008 784

(51) Int. Cl.
*A61F 2/958* (2013.01)
*A61M 25/10* (2013.01)
*A61F 2/07* (2013.01)

(52) U.S. Cl.
CPC ......... *A61F 2/958* (2013.01); *A61M 25/1011* (2013.01); *A61F 2/07* (2013.01); *A61M 25/104* (2013.01); *A61M 2025/105* (2013.01)

(58) Field of Classification Search
CPC ....... A61F 2/958; A61F 2/07; A61M 25/1011; A61M 2025/105; A61M 25/104
See application file for complete search history.

(56) References Cited

U.S. PATENT DOCUMENTS

| 3,409,015 A | 11/1968 | Swanson |
| 4,423,725 A * | 1/1984 | Baran ............... A61M 16/0479 128/207.15 |
| 4,546,759 A * | 10/1985 | Solar .................. A61M 1/1072 600/18 |
| 4,744,366 A | 5/1988 | Jang et al. |
| 5,019,042 A * | 5/1991 | Sahota ............. A61M 25/1002 604/101.01 |

(Continued)

FOREIGN PATENT DOCUMENTS

| DE | 3 779 539 | 2/1993 |
| DE | 6 982 7982 | 12/2005 |

(Continued)

OTHER PUBLICATIONS

International Preliminary Report on Patentability for PCT/EP2016/066581, dated Jan. 16, 2018, 6 pages.

(Continued)

*Primary Examiner* — Phong Son H Dang
(74) *Attorney, Agent, or Firm* — Rimon, P.C.

(57) ABSTRACT

The present invention relates to a catheter comprising a balloon, wherein said catheter comprises the following: a dilatation body and a catheter shaft which comprises a proximal and a distal end; the catheter shaft additionally comprising a fluid lumen by means of which a fluid can be fed to said dilatation body. The dilatation body is made up of at least three balloon segments which are arranged immediately adjacently to one another and one being the other on said catheter shaft, and can be dilated independently of one another.

15 Claims, 3 Drawing Sheets

(56) References Cited

U.S. PATENT DOCUMENTS

| | | | | |
|---|---|---|---|---|
| 5,545,209 | A | * | 8/1996 | Roberts .................. A61F 2/958 604/103.05 |
| 5,588,965 | A | * | 12/1996 | Burton ............... A61M 25/1011 604/101.05 |
| 5,725,535 | A | | 3/1998 | Hedge et al. |
| 5,800,393 | A | * | 9/1998 | Sahota .................... A61F 2/958 604/103.07 |
| 5,863,285 | A | | 1/1999 | Coletti |
| 5,899,917 | A | * | 5/1999 | Edwards ................ A61L 31/18 606/195 |
| 5,951,514 | A | * | 9/1999 | Sahota .................... A61F 2/958 604/101.05 |
| 6,148,222 | A | * | 11/2000 | Ramsey, III ......... A61N 1/0517 600/380 |
| 6,527,739 | B1 | | 3/2003 | Bigus et al. |
| 6,682,555 | B2 | * | 1/2004 | Cioanta ................. A61B 18/04 604/101.03 |
| 6,716,252 | B2 | * | 4/2004 | Lazarovitz ......... A61M 25/1011 604/8 |
| 6,796,960 | B2 | * | 9/2004 | Cioanta ................. A61B 18/04 604/103.01 |
| 7,740,609 | B2 | * | 6/2010 | Rowe ................ A61M 25/1011 604/101.05 |
| 8,814,826 | B2 | * | 8/2014 | Foreman ........... A61M 25/1011 604/96.01 |
| 2002/0055709 | A1 | | 5/2002 | Weinberger |
| 2002/0165521 | A1 | * | 11/2002 | Cioanta ................. A61B 18/04 604/509 |
| 2004/0230316 | A1 | * | 11/2004 | Cioanta ............. A61B 18/1492 623/23.66 |
| 2006/0129093 | A1 | * | 6/2006 | Jackson ............. A61M 25/1011 604/96.01 |
| 2008/0249461 | A1 | * | 10/2008 | Foreman ........... A61M 25/1002 604/28 |
| 2008/0300539 | A1 | * | 12/2008 | Vreeman ........... A61M 25/0054 604/103.06 |
| 2011/0218494 | A1 | * | 9/2011 | Gerrans ......... A61B 17/320725 604/101.05 |
| 2012/0323211 | A1 | | 12/2012 | Ogle et al. |
| 2013/0053758 | A1 | * | 2/2013 | Kibbe .................... A61L 31/16 604/21 |
| 2013/0345628 | A1 | * | 12/2013 | Berger ................ A61M 25/007 604/101.05 |
| 2015/0005693 | A1 | * | 1/2015 | Gerrans ............. A61B 17/3205 604/20 |

FOREIGN PATENT DOCUMENTS

| | | |
|---|---|---|
| JP | 2001-500761 A | 1/2001 |
| WO | 9811935 A1 | 3/1998 |
| WO | WO-00/27454 | 5/2000 |

OTHER PUBLICATIONS

International Search Report and Written Opinion for PCT/EP2016/066581, dated Oct. 4, 2016, 14 pages.

CN, 1st Office Action for CN patent application 291680041269.1, dated Nov. 26, 2018, 10 pages with additional 10 pages of an English language equivalent or summary.

JP, Notice of Reason for Refusal for JP patent application 2018-500795, dated Dec. 25, 2018, 5 pages with additional 4 pages of an English language equivalent or summary.

* cited by examiner

BALLOON CATHETER

CROSS REFERENCES TO RELATED APPLICATIONS

This application is a continuation of international patent application PCT/EP2016/066581, filed on Jul. 13, 2016 designating the U.S., which international patent application has been published in German language and claims priority from German patent application DE 10 2015 008 784.3, filed on Jul. 13, 2015. The entire contents of these priority applications are incorporated herein by reference.

BACKGROUND OF THE INVENTION

The present invention relates to a catheter for expanding and releasing an expandable endoluminal prosthesis, said catheter having a dilation body, whose dilation permits the expansion of the stent, and moreover a catheter shaft with a proximal first end and a distal end, said catheter shaft having a fluid lumen via which a fluid can be delivered to the dilation body, and the dilation body being mounted on the catheter shaft in such a way that it is dilatable by delivery of a fluid.

Catheters of this kind are known in the prior art and are used for the expansion of an expandable endoluminal prosthesis, for example in blood vessels.

The use of expandable endoluminal prostheses of this kind, which are also designated as stents or stent grafts, is known in the prior art, for example in cases of vascular constriction. The constricted or occluded blood vessels are widened or re-opened by means of balloon dilation or by other methods.

More severe blockage of the blood vessels of affected patients may lead to hypertension, ischemic damage, stroke or myocardial infarction. Atherosclerotic lesions, which restrict or block coronary blood flow, are the main cause of ischemic heart disease.

The balloon catheters are almost always introduced into the stenosed region from the direction of the groin, via a guidewire and guide catheter, and are inflated by pressure. In this way, the constriction is eliminated and an operation avoided. In addition, as has been mentioned above, stents (wire meshes intended to splint the vessel from inside and keep it open) or stent grafts (wire meshes with a cover) are often implanted.

However, stents and stent grafts are also used in the treatment of aneurysms, for example. An aneurysm is understood here as a widening or bulging of a blood vessel as a consequence of congenital or acquired lesions of the wall. The bulge in this case can affect the vessel wall as a whole or, in what is called a false aneurysm or dissection, blood flows from the lumen of the vessel in between the layers of the vessel wall and tears these apart from one another. Non-treatment of an aneurysm may lead to a rupture of the blood vessel in advanced stages, after which the patient suffers internal bleeding.

The stents/stent grafts or vascular prostheses used for the treatment of vascular constrictions generally consist of a tubular/hollow cylindrical metal framework or of individual metal (stent) springs which are arranged one behind another and of which the jacket surface is covered, in the case of stent grafts, by a textile or polymer film, such that a hollow cylindrical body is obtained. For this purpose, the stent/stent graft is generally loaded in the crimped state onto a balloon catheter and brought by means of a guidewire into the region of the lesion where the stent is intended to be released. For this purpose, the balloon, and with it the stent or stent graft, is expanded and pressed against the vessel wall. The stent/stent graft is thus plastically deformed and remains in this expanded state, in which it has a greater diameter than in the loaded state on the balloon catheter. In this way, the lesion is also kept open and the object of the therapy is achieved. After the expansion of the stent/stent graft, the balloon catheter is deflated again and removed from the vessel.

During dilation of a stent/stent graft, some balloon catheters known in the prior art are subjected to a high hydraulic pressure of up to 30 bar. This is achieved technically by using what are called non-compliant balloons, i.e. structures made of extremely stable film tubes which resist such pressures and which cannot be expanded any further than their nominal diameter. This is an important safety aspect in preventing overexpansion of the vessel.

The disadvantage of such a structure is that the balloon catheter in the dilated state always has to be straight on account of its high internal pressure. However, vascular anatomy often requires a curved or flexible arrangement. This situation is very disadvantageous especially in the case of longer lesions, since the vessel is forced into the straight shape of the stent and also remains in this shape.

The object of the present invention is therefore to make available a system with which the disadvantages described above can be overcome.

SUMMARY OF THE INVENTION

According to the invention, this object is achieved by a catheter for expanding and releasing an expandable endoluminal prosthesis, said catheter having the following: a dilation body whose dilation permits the expansion of an expandable prosthesis, a catheter shaft with a proximal first end and a distal end, said catheter shaft having a fluid lumen via which a fluid can be delivered to the dilation body; moreover, the dilation body is mounted on the catheter shaft in such a way that it is dilatable by delivery of a fluid; the catheter according to the invention is characterized in that the dilation body is formed by at least three balloon segments which are arranged immediately adjacent to one another and one behind the other on the catheter shaft and are dilatable independently of one another.

The object of the invention is moreover achieved by using the catheter according to the invention in combination with a stent or stent graft for the treatment of vascular lesions, aneurysms or stenoses.

The object of the invention is thereby achieved in full.

With the catheter according to the invention, the total length of which has or consists of several segments, i.e. at least three segments, with individually fillable and expandable or dilatable balloons, it is possible that the expandable stent/stent graft to be used can also be expanded in a curved vessel without causing traumatic change to the latter. This is achieved by the segmentation of the dilation body of the catheter and by the fact that these segments are controllable individually and sequentially.

The balloon segments are by definition arranged immediately adjacent to one another and one behind the other and thus form individual or individually inflatable/dilatable and individually controllable segments which, if appropriate, may be in contact with each other via their respective ends.

According to one aspect of the catheter according to the invention, said catheter accordingly has a fluid lumen via which a fluid can be delivered in sequence to the balloon segments. In this embodiment, a fluid is thus delivered to the balloon segments via one fluid lumen, in which case suitably provided seals and/or valves ensure that the balloon segments can be controlled and dilated in sequence. Provision can be made, for example, that a predetermined quantity of fluid is delivered to a respective balloon segment before an optionally defined quantity of fluid is delivered to the balloon segment that is arranged immediately downstream in the sequence.

According to a further aspect of the catheter according to the invention, said catheter has a fluid lumen for each of the balloon segments, by way of which a fluid can be delivered to each of the balloon segments. Therefore, in this embodiment, each balloon segment is assigned a fluid lumen via which the balloon segments are controllable individually and sequentially.

In the present case, the fluid can be a gas or a liquid, e.g. saline, or an radio-opaque contrast medium, and any fluid customarily used in this field for the dilation of dilation bodies, in which connection many possibilities will be known to a person skilled in the art. Said person skilled in the art will take into account the fact that dilation and deflation can be effected more quickly with gas than with a liquid. The fluid lumen can run through the entire catheter shaft or only the region of the balloon segments. The fluid lumen is in contact with the balloon segments via openings or delivery lines, each balloon segment having its own opening through which the fluid is delivered. An "opening" is understood as any fluid connection between the interior of a balloon segment, e.g. a bore, opening or an access point, and the lumen of the fluid lumen.

According to a further aspect, the balloon segments each have two end portions via which they are fixed on the catheter shaft, and they each have a middle/central portion which extends between the two end portions, is not fixed on the catheter shaft and is dilatable by delivery of a fluid.

According to the invention, it is preferable if at least three, preferably between 3 and 15, in particular 4, 5, 6, 7, 8, 9, 10, 11, 12, 13, 14 or 15 balloon segments are provided, to which a fluid can be delivered via one or more fluid lumens.

A person skilled in the art will be able to determine the specific number of balloon segments on the basis of the present teaching and in consideration of the stent/stent graft to be used and of the particular vascular anatomy of a patient.

In the catheter according to the invention, it is moreover preferable if an individual balloon segment has a length of at least 3 mm, in particular at least 5 mm or 7 mm, and preferably at least 10 mm and at most 20 mm.

The diameter of the balloon is preferably between 5 and 20 mm.

As regards the lengths of the balloon segments too, a person skilled in the art will be able to determine sizes and dimensions suitable for the particular patient or for the particular vessel section to be treated, specifically on the basis of the present teaching and in consideration of the number of balloon segments.

According to one aspect of the present invention, the catheter shaft moreover has a guidewire lumen, which is different than the fluid lumen.

According to a further aspect of the catheter according to the invention, the balloon segments each have a wall, of which the wall thickness is in each case uniform or non-uniform over the portions of an individual balloon segment. In this embodiment, it is advantageously possible to take into account that the wall thickness of the balloon segment portion coming to bear on the respectively adjacent balloon can be differently configured, i.e. smaller or greater, than the wall thickness of the balloon segment portions that press against the vessel wall, or, alternatively, the wall thickness of a balloon segment can be identical over its entire length and in all its respective portions. Different balloon segments can also have different or identical wall thicknesses across their respective portions.

According to a further aspect of the catheter according to the invention, the balloon segments each have a wall with a wall thickness, the wall thicknesses of the balloon segments being different or uniform. In this embodiment, it is thus advantageously possible to take into account if the balloon segments which are arranged behind one another along the length of the catheter have different wall thicknesses from each other, such that here too it is possible to consider optional adaptation to different vessel anatomies.

Moreover, such balloon segments having different wall thicknesses can in turn have different wall thicknesses in relation to their respective portions.

In a development of the catheter according to the invention, it is preferable if the outer surface of the balloon segments is coated with a substance chosen from: a medicament, a hydrophilic coating, a heparin coating or a combination thereof.

Coated balloon catheters are known in the prior art. Any pharmaceutical substance, e.g. rapamycin, paclitaxel or the like, which assists or promotes the patency of the affected vessel can in principle be taken into consideration as a coating.

In principle, the present invention also relates to the use of the catheter according to the invention in angioplasty, i.e. in a method for the treatment of stenoses, which treatment takes place without the release of a stent/stent graft. All of the above comments concerning the catheter according to the invention for the expansion of an expandable endoluminal prosthesis thus apply expressly to a catheter according to the invention for the treatment of stenoses. In this embodiment, the dilation body is designed in such a way that it is suitable for the dilation of a stenosis in a blood vessel.

According to the invention, the dilation segments according to a preferred embodiment are balloon segments.

In the present case, a "balloon" is understood as any elastic sheath which, at least in the filled state, is self-supporting and gas-tight/liquid-tight and which has a substantially bulbous shape that can be filled with a fluid, i.e. a gas or a liquid. The sheath can have a symmetrical or asymmetrical shape.

According to one aspect, it is preferable if the balloon segments, in the dilated state, each have a shape chosen from substantially round or egg-shaped/oval. The shape of the balloon segments is generally predefined by the respective materials from which the balloon segments are formed, wherein the balloon segments are accordingly made from what is called a non-compliant, i.e. material that cannot be dilated/expanded beyond a defined end dimension.

According to an aspect, it is preferable if the shape of the balloon segments is elongate, with a first end and a second end, wherein "elongate" includes any shape that is longer in the axial direction than in the radial direction. In this embodiment, the proximal end of a balloon segment, for example, can curve outward, and the distal end can curve inward, wherein an outwardly curved proximal end of a second balloon segment arranged behind a first balloon segment engages in the inwardly directed curvature of the first balloon segment. Here, "inward" and "outward" always relate to the individual body of a balloon segment. According to a further embodiment, the balloon segment arranged farthest distally, for example, has an outwardly directed curvature at its two ends, since no further balloon segment engages in the second end thereof.

Here, a "dilation body" is understood as any elastic element which, by application of pressure, for example by delivery of a fluid, is able to increase in volume or expand.

According to a development of the catheter according to the invention, a sealing element is provided in the fluid lumen and controls the individual dilation segments.

According to a further aspect, provision is made that the sealing element is designed to be controllable laterally in the fluid lumen.

As has already been mentioned in the introduction, the present invention also relates to the use of an above-described catheter, for the release of an expandable endoluminal prosthesis in a vessel of a patient for treatment of a vascular constriction, and to the above-described catheter according to the invention with an expandable endoluminal prosthesis loaded or mounted thereon.

The present invention moreover relates to a method for releasing an expandable endoluminal prosthesis in a vessel of a patient, which method has the following steps:
  a) making available an expandable endoluminal prosthesis mounted on a catheter according to the invention;
  b) inserting the catheter, loaded with the expandable endoluminal prosthesis, as far as the site that is to be treated in the vessel;
  c) dilating the balloon segments in sequence for the expansion and release of the expandable endoluminal prosthesis in the vessel.

According to an aspect of the method according to the invention, it is preferable if the expandable endoluminal prosthesis is released at a site in the vessel where there is a curvature.

The vessel is preferably a blood vessel or another hollow organ of a preferably human patient, e.g. also the bile duct or the urethra.

The present invention moreover also relates to a method for treating a stenosis in a vessel, preferably a blood vessel or another hollow organ of a patient, preferably a human, which method has the following steps:
  a) making available a catheter according to the invention, which is optionally loaded with an expandable endoluminal prosthesis;
  b) inserting the catheter from step a) as far as the site that is to be treated in the vessel;
  c) dilating the balloon segments in sequence, thereby expanding and releasing the expandable endoluminal prosthesis in the vessel, for the treatment of stenosis, in such a way that the vessel is widened or re-opened.

The material from which the balloon segments of the catheter according to the invention are made or as such have is preferably a polymer, e.g. chosen from the group including polyurethane, polyether polyurethane, polyethylene terephthalate, polybutylene terephthalate, polyamide and copolymers and mixtures thereof.

In the embodiments in which the balloon is coated, the pharmaceutical active substance can also ready be contained in the polymer from which the balloon segments are formed. Alternatively, the pharmaceutical active substance can also be applied to the dried and/or cleaned balloon segment, in which case it is intended to be applied preferably in the expanded state of the balloon segment. The active substance or the active substance composition ideally has only minimal interactions with the polymer membrane of the balloon segment in order to facilitate the release of the active substance.

Further advantages and features will become clear from the following description and the attached drawing.

It will be appreciated that the aforementioned features and the features still to be explained below can be used not only in the respectively cited combination but also in other combinations or singly, without departing from the scope of the present invention.

BRIEF DESCRIPTION OF THE DRAWINGS

An illustrative embodiment of the invention is shown in the drawing and is described in more detail below with reference to said drawing, in which.

DESCRIPTION OF PREFERRED EMBODIMENTS

Figure 1:
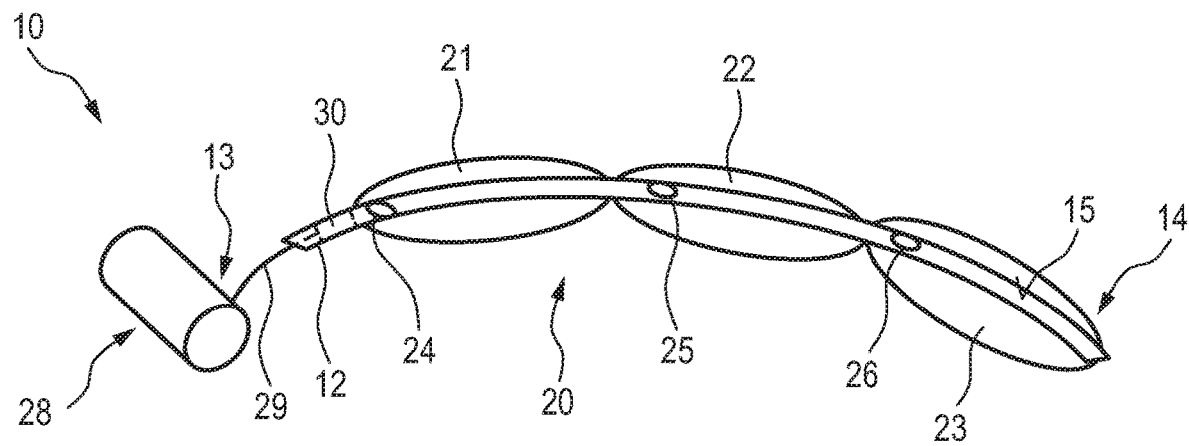
FIG. 1 shows a schematic view of a first embodiment of a catheter according to the invention, before the start of the dilation of the balloon segments (without prosthesis loading)

In FIGS. 1 to 4, reference sign 10 designates an illustrative embodiment of a catheter according to the invention, having a catheter shaft 12 with a proximal first end 13 and a distal end 14, said catheter shaft 12 having a fluid lumen 15.

The catheter 10 according to the invention in FIG. 1 moreover has a dilation body 20 which, in the example shown in FIG. 1, is composed of 3 separate balloon segments 21, 22, 23 which are arranged immediately adjacent to one another and one behind the other and are dilatable independently of one another. The shape of the balloon segments shown in FIGS. 1 to 4 is substantially round or oval. It will be appreciated that the catheter according to the invention can also have more than three balloon segments.

As is shown in FIGS. 1 to 4, the individual balloon segments have a "substantially" round or oval shape in the sense that they do not need to have an identical shape in the expanded state, but a shape nonetheless that has the essential features of the respective other shapes.

In the fluid lumen 15, openings 24, 25, 26 are provided, through each of which fluid can be delivered to the balloon segments 21, 22 and 23.

The catheter 10 according to the invention shown in FIGS. 1 to 4 moreover has, at its proximal end 13, a control means 28 via which the delivery of the fluid to the individual balloon segments 21, 22, 23 can be controlled.

Figure 2:
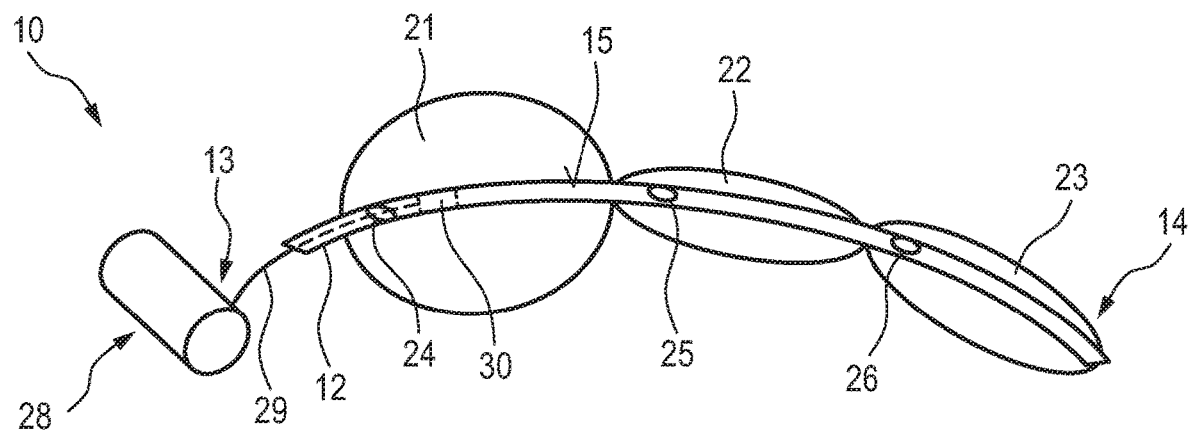
FIG. 2 shows the schematic view of the first embodiment from FIG. 1, with the proximally situated balloon segment here shown in the dilated state.
Figure 3:
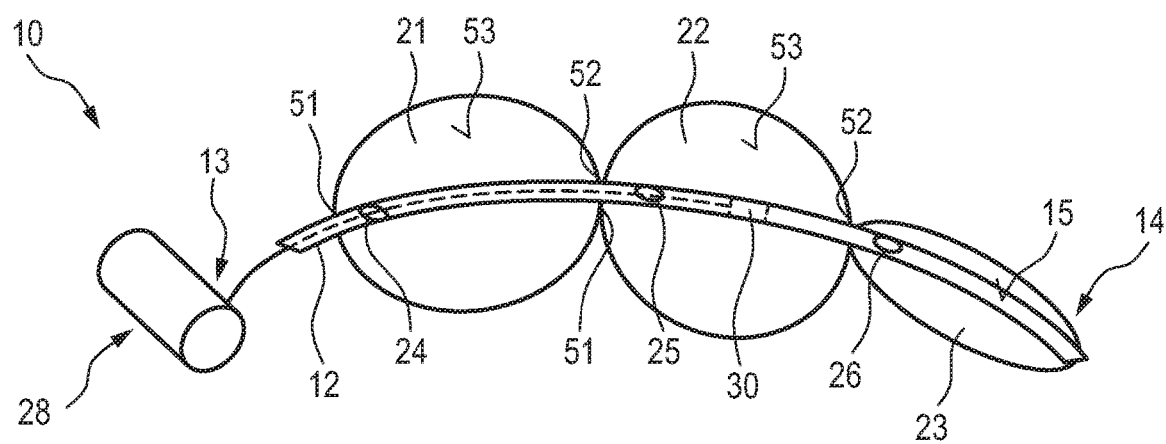
FIG. 3 shows the schematic view of the first embodiment from FIGS. 1 and 2 in a state in which the balloon segment situated between the proximal and distal balloon segments is shown in a dilated state.
Figure 4:
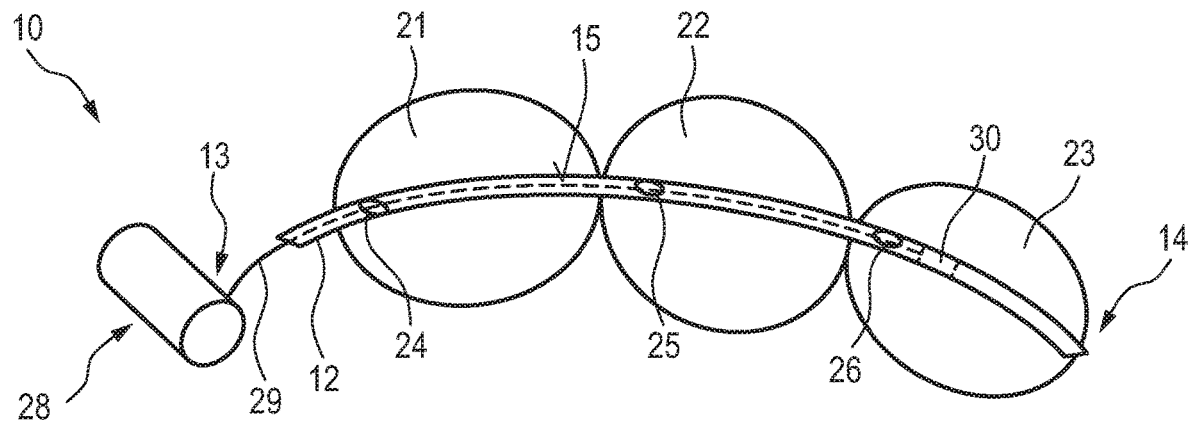
FIG. 4 shows the schematic view of the first embodiment from FIGS. 1 to 3 in a state in which all the balloon segments are dilated.

According to the embodiment shown in FIGS. 1 to 3, which is shown in FIGS. 1 to 4 in different dilated states of the balloon segments, the control means 28 comprises a control cable 29 and a sealing element 30 with which the delivery lines to the individual balloon segments can be sealed off as soon as the desired dilation state of a respective balloon segment is reached.

As can be seen from FIGS. 1 to 4, by moving the sealing element 30 in the distal direction, i.e. away from the user, the delivery of the fluid for dilation of the individual balloon segments can be controlled by the sealing element 30 sealing off the delivery line or openings 24, 25 and 26 of the respective delivery balloon segments 21, 22 and 23 as soon as the seal passes these openings 24, 25 and 26 in the distal direction.

In this way, sequential filling and dilation of the balloon segments 21, 22 and 23 can be achieved.

Alternatively, the control can also be effected such that the delivery lines or openings 24, 25, 26 to the respective balloon segments 21, 22, 23 are opened only when the sealing element 30 has passed each of these.

Since they are each designed as non-compliance balloon segments 21, 22, 23, they are able to dilate only as far as a spatially predetermined expansion.

Referring to FIG. 3 by way of example, it will also be seen that each of the balloon segments 21, 22, 23 has two respective end portions 51, 52, via which the balloon segments 21, 22, 23 are fixed on the catheter shaft, and a central portion 53, which is not fixed on the catheter shaft and is dilatable by delivery of a fluid.

The control can take place from proximal to distal or from distal to proximal, likewise the dilation of the individual balloon segments 21, 22, 23, which can accordingly be dilated in sequence from proximal to distal or from distal to proximal.

FIG. 5, finally, shows a further embodiment of a catheter 100 according to the invention, having a catheter shaft 112 with a proximal first end 113 and a distal end 114, said catheter shaft 112 having a fluid lumen 115.

The catheter 110 according to the invention in FIG. 5 moreover has a dilation body 120 which, in the example shown in FIG. 5, is composed of 3 separate balloon segments 121, 122, 123 which are arranged immediately adjacent to one another and one behind the other and are dilatable independently of one another. The shape of a balloon segment 121, 122, 123 in the embodiment shown in FIG. 5 is elongate, specifically such that each one has a first end 141 and a second end 142. The first end 141 curves outward in the expanded state, in relation to the respective balloon segment 121, 122, 123, and the second end 142 curves inward in the expanded state, likewise in relation to the same respective balloon segment 121, 122, 123. An outwardly curved first end 141 of a second balloon segment 122 arranged behind a first balloon segment 121 engages in the inwardly directed curvature of the first balloon segment 121.

In the fluid lumen 115, openings 124, 125, 126 are provided, through each of which a fluid can be delivered to the balloon segments 121, 122 and 123.

Figure 5A:
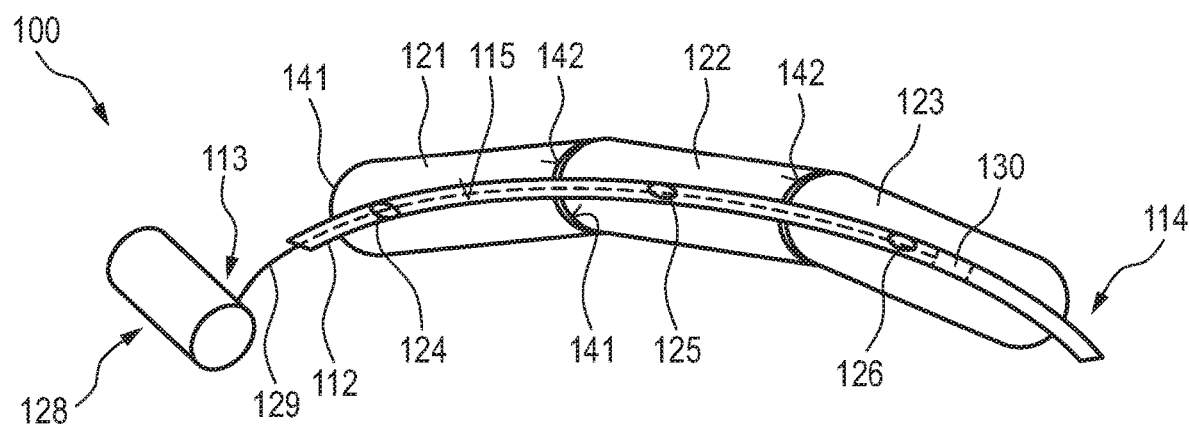
FIG. 5 shows a schematic view of a further embodiment of a catheter according to the invention (A); and a schematic detail of a balloon segment (B).
Figure 5B:
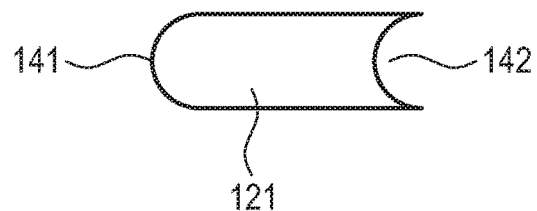

The catheter 110 according to the invention shown in FIG. 5A moreover has, at its proximal end 113, a control means 128 via which the delivery of the fluid to the individual balloon segments 121, 122, 123 can be controlled.

According to the embodiment shown in FIG. 5A, the control means 128 likewise comprises a control cable 129 and a sealing element 130 with which the delivery lines or openings 124, 125 and 126 to the individual balloon segments 121, 122, 123 can be controlled and for example sealed off as soon as the desired dilation state of a respective balloon segment 121, 122, 123 is reached.

As can also be seen from FIG. 5A, the balloon segment 123, which is arranged farthest distally, has an elongate balloon shape with a first end and a second end, which each curve outward. This element is shown in more detail in FIG. 5B.

For the use of the illustrative embodiments of the catheter 10, 100 according to the invention, said catheter 10, 100 is either loaded with an expandable prosthesis, for example a stent/stent graft (not shown), in which case the expandable stent/stent graft is generally crimped on, and is advanced to the desired site in the vessel, preferably via a guidewire. As soon as the stent/stent graft is positioned at the desired site, preferably in a curvature of a vessel, the balloon segments 21, 22, 23 or 121, 122, 123 are dilated one after another in sequence by delivery of a fluid, specifically in the order in which they are arranged behind one another. In this way, they press the expandable stent/stent graft radially outward and against the vessel wall, as a result of which the latter is supported or re-opened.

As soon as the stent/stent graft is expanded, the balloon segments are deflated again and the catheter 10, 100 is removed from the vessel, whereas the stent/stent graft remains in the vessel.

What is claimed is:

1. A catheter for expanding an expandable endoluminal prosthesis, said catheter having the following:
   a dilation body whose dilation permits the expansion of an expandable prosthesis optionally loaded on the catheter,
   a catheter shaft with a proximal first end and a distal end, said catheter shaft having a fluid lumen via which a fluid can be delivered to the dilation body,
   the dilation body being mounted on the catheter shaft in such a way that it is dilatable by delivery of a fluid, characterized in that the dilation body is formed by at least three balloon segments which are arranged immediately adjacent to one another and one behind the other on the catheter shaft and are dilatable independently of one another, and that a sealing element is provided in the fluid lumen and the sealing element controls delivery of the fluid to and from the at least three balloon segments individually.

2. The catheter as claimed in claim 1, characterized in that the fluid lumen is a single fluid lumen via which a fluid can be delivered in sequence to the balloon segments.

3. The catheter as claimed in claim 1, characterized in that the fluid lumen include openings for each of the balloon segments, via which the fluid can be delivered to each of the balloon segments.

4. The catheter as claimed in claim 1, characterized in that the balloon segments each has two end portions via which they are fixed on the catheter shaft, and they each has a central portion, which extends between the two end portions, that is not fixed on the catheter shaft and is dilatable by delivery of a fluid.

5. The catheter as claimed in claim 1, characterized in that between 3 and 15 balloon segments are provided, to which a fluid can be delivered via the fluid lumen.

6. The catheter as claimed in claim 1, characterized in that an individual balloon segment has a length of at least 3 mm, in particular at least 5 mm and preferably at least 10 mm.

7. The catheter as claimed in claim 1, characterized in that the balloon segments each have a wall, of which the wall thickness is in each case uniform or non-uniform over the portions of an individual balloon segment.

8. The catheter as claimed in claim 1, characterized in that the balloon segments each have a wall with a wall thickness, the wall thicknesses of the balloon segments being different or uniform.

9. The catheter as claimed in claim 1, further characterized in that the balloon segments each has an outer surface, and the outer surface of each of the balloon segments is coated with a substance chosen from: a pharmaceutical active substance, a hydrophilic coating, a heparin coating or a combination thereof.

10. The catheter as claimed in claim 1, characterized in that the sealing element is designed to control delivery of the fluid from the proximal end to the distal end or from the distal end to the proximal end.

11. The catheter as claimed in claim 1, characterized in that the catheter moreover has an expandable endoluminal prosthesis loaded thereon.

12. Method for treating a vascular constriction of a vessel of patient in need thereof, the method comprising the steps of
    a) making available an expandable endoluminal prosthesis mounted on a catheter as claimed in claim 1;
    b) inserting the catheter, loaded with the expandable endoluminal prosthesis, as far as the site that is to be treated in the vessel;
    c) dilating the balloon segments in sequence for expansion and release of the expandable endoluminal prosthesis in the vessel,
thereby treating the vascular constriction.

13. The method as claimed in claim 12, characterized in that the expandable endoluminal prosthesis is released at a site in the vessel where there is a curvature.

14. A method for releasing an expandable endoluminal prosthesis in a vessel of a patient, which method has the following steps:
    a) making available an expandable endoluminal prosthesis mounted on a catheter as claimed in claim 1;
    b) inserting the catheter, loaded with the expandable endoluminal prosthesis, as far as the site that is to be treated in the vessel;
    c) dilating the balloon segments in sequence for expansion and release of the expandable endoluminal prosthesis in the vessel.

15. The method as claimed in claim 14, characterized in that the expandable endoluminal prosthesis is released at a site in the vessel where there is a curvature.

\* \* \* \* \*